US012788219B2

(12) United States Patent
Wu et al.

(10) Patent No.: US 12,788,219 B2
(45) Date of Patent: Nov. 10, 2026

(54) ENDOSCOPIC LIGHT SOURCE-IMAGING MODULE AND METHOD FOR FABRICATING THE SAME

(71) Applicant: Medimaging Integrated Solution, Inc., Hsinchu (TW)

(72) Inventors: Shangyi Wu, Hsinchu (TW); Jia-De Zhou, Hsinchu (TW)

(73) Assignee: Medimaging Integrated Solution, Inc., Hsinchu (TW)

( * ) Notice: Subject to any disclaimer, the term of this patent is extended or adjusted under 35 U.S.C. 154(b) by 451 days.

(21) Appl. No.: 18/330,098

(22) Filed: Jun. 6, 2023

(65) Prior Publication Data

US 2024/0065532 A1 Feb. 29, 2024

(30) Foreign Application Priority Data

Aug. 25, 2022 (TW) ................................. 111131979

(51) Int. Cl.
*A61B 1/00* (2006.01)
*A61B 1/04* (2006.01)
*A61B 1/06* (2006.01)

(52) U.S. Cl.
CPC ........ *A61B 1/0011* (2013.01); *A61B 1/00114* (2013.01); *A61B 1/04* (2013.01); *A61B 1/06* (2013.01)

(58) Field of Classification Search
CPC ................ B29C 45/13; B29C 45/1866; B29C 2045/14368; B29C 2045/14967; B29C 2045/14139
See application file for complete search history.

(56) References Cited

U.S. PATENT DOCUMENTS 6,264,869 B1 * 7/2001 Notarpietro ............. B44C 3/046 264/273
11,309,299 B2 * 4/2022 Wu ........................ H05K 1/189
2009/0277684 A1 * 11/2009 Takahashi ........... H01L 23/3135 174/565
2013/0309341 A1 * 11/2013 Kato .................. B29C 45/1459 425/126.1
2019/0246027 A1 * 8/2019 Kuhn .................. A61B 1/0011
(Continued)

FOREIGN PATENT DOCUMENTS

JP 6597594 B2 * 10/2019 ............... H02K 1/28
WO WO-2010066790 A1 * 6/2010 ........... A61B 1/0676

*Primary Examiner* — Emmanuel S Luk
(74) *Attorney, Agent, or Firm* — MUNCY, GEISSLER, OLDS & LOWE, P.C.

(57) ABSTRACT

An endoscopic light source image module comprises a substrate, an image sensor, an illumination module and a single-use mold. The image sensor, the illumination module and the single-use mold are disposed on the substrate. The illumination module includes a carrier disposed on the substrate and a light source disposed on the carrier, wherein the carrier is used to determine the height of the light source. The single-use mold has a first through-hole, a second through-hole and a runner, wherein the first through-hole accommodates the image sensor; the second through-hole accommodates the illumination module; the runner interconnects the first through-hole and the second through-hole. The single-use mold is made of an opaque material, which can prevent the light of the illumination module from affecting the image sensor.

8 Claims, 10 Drawing Sheets

(56) References Cited

U.S. PATENT DOCUMENTS

| | | | | |
|---|---|---|---|---|
| 2019/0315027 | A1* | 10/2019 | Sugiyama | B29C 45/14 |
| 2020/0008658 | A1* | 1/2020 | Hayakawa | A61B 1/0011 |
| 2020/0047383 | A1* | 2/2020 | Otsuka | B29C 45/1675 |
| 2022/0265122 | A1* | 8/2022 | Cheng | A61B 1/05 |
| 2022/0330798 | A1* | 10/2022 | Hedemann | G02B 23/2469 |
| 2023/0007769 | A1* | 1/2023 | Yamada | A61B 1/00096 |
| 2024/0038817 | A1* | 2/2024 | Yamada | H10F 39/811 |
| 2024/0235347 | A1* | 7/2024 | Claassen | B29C 45/03 |
| 2025/0072722 | A1* | 3/2025 | Wu | B29C 33/0022 |

* cited by examiner

ENDOSCOPIC LIGHT SOURCE-IMAGING MODULE AND METHOD FOR FABRICATING THE SAME

BACKGROUND OF THE INVENTION

1. Field of the Invention

The present invention relates to an endoscopic light source-imaging module, particularly to a small-sized and easy-to-assemble light source-imaging module and a method for fabricating the same.

2. Description of the Prior Art

In the conventional endoscope, the light source-imaging module is disposed on a printed circuit board (PCB) or a flexible printed circuit (FPC). The light source-imaging module may be a CMOS image sensor (CIS) module. FIG. 1 and FIG. 2 schematically show a conventional light source-imaging module 10, which comprises an image sensing device 11, an illumination module 12, and a substrate 13. The region of the substrate 13 which the image sensing device 11 and the illumination module 12 are disposed on, is bent to a predetermined angle to form the light source-imaging module 10 shown in FIG. 1. The image sensing device 11 includes a sensor 112 and a light shielding cap 114. The light shielding cap 114 covers the lateral sides of the sensor 112 to prevent the light of the illumination module 12 from entering the sensor 112. The relative height of the image sensing device 11 and the illumination module 12 may be adjusted via varying the bending angle, whereby to optimize light source parameters and illumination parameters. The external control circuit (not shown in the drawing) of the light source-imaging module 10 is electrically connected with the image sensor 11 and the illumination module 12 through the transmission cables 14 coupled to the substrate 13, whereby the control circuit can control the operation of the image sensing device 11 and the illumination module 12. After the image sensing device 11, the illumination module 12 and the transmission cables 14 have been soldered or glued to the substrate 13, a plastic material is injected in an insert-molding method or an over-molding method to form a casing 15 wrapping the light source-imaging module 10, as shown in FIG. 2. In addition to the abovementioned injection-molding methods, the light source-imaging module 10 may be sleeved by a hollow pipe (casing), and a resin is fully filled into the hollow pipe to fix the light source-imaging module 10 inside the hollow pipe.

The substrate 13 of the light source-imaging module 10 needs bending to adjust the heights of the image sensing device 11 and the illumination module 12. However, such a requirement makes the light source-imaging module 10 larger in size and hard to assemble. Besides, a resin must be filled into the region between the sensor 112 and the light shielding cap 114 to secure the sensor 112 and the light shielding cap 114. Thus, a sufficient space should be reserved to allow a resin-filling needle to deep reach the abovementioned region for resin filling. Then is further increased the size of the light source-imaging module 10. In other words, the conventional light source-imaging module 10 is too large to be used in a small-size endoscope. In addition the region between the sensor 112 and the light shielding cap 114, the recessed region (not shown in the drawing) of the illumination module 12 also needs filling with resin for structural security. In other words, the conventional light source-imaging module 10 needs several cycles of resin filling processes and thus suffers poor production efficiency.

SUMMARY OF THE INVENTION

One objective of the present invention is to provide an endoscopic light source-imaging module and a method for fabricating the same.

Another objective of the present invention is to provide a small-sized and easy-to-assemble endoscopic light source-imaging module and a method for fabricating the same.

According to one embodiment, the endoscopic light source-imaging module of the present invention comprises a substrate, an image sensor, an illumination module, and a single-use mold. The image sensor, the illumination module and the single-use mold are disposed on the substrate. The illumination module includes a carrier disposed on the substrate and a light source disposed on the carrier, wherein the carrier is used to determine the height of the light source. The single-use mold includes a first through-hole, a second through-hole, and a runner, wherein the first through-hole accommodates the image sensor; the second through-hole accommodates the illumination module; the runner interconnects the first through-hole and the second through-hole. The single-use mold is made of an opaque material lest the light of the illumination module affects the image sensor.

According to one embodiment, a method for fabricating an endoscopic light source-imaging module of the present invention comprises steps: providing a substrate, which includes a front surface, a rear surface, a first metal route, and a second metal route, wherein the first route and the second route extend from the front surface to the rear surface; fixing an image sensor onto the front surface and electrically connecting the image sensor with the first metal route; disposing an illumination module on the front surface and electrically connecting the illumination module with the second metal route; and disposing a single-use mold on the front surface, wherein the single-use mold includes a first through-hole and a second through-hole respectively accommodating the image sensor and the illumination module; the single-use mold also includes a runner interconnecting the first through-hole and the second through-hole.

In the present invention, the difference of the heights of the image sensor and the illumination module can be varied via changing the height of the carrier of the illumination module. It is unnecessary for the present invention to bend the substrate for adjusting the height difference. Therefore, the present invention can reduce the size of the light source-imaging module and make the light source-imaging module assembled easily. In the light source-imaging module of the present invention, a resin material may be filled from the second through-hole and then flows to the first through-hole via the runner. Therefore, it is unnecessary for the present invention to preserve a space allowing the resin-filling needle to enter the region between the first through-hole and the image sensor. Therefore, the size of the light source-imaging module is further reduced. Because of only needing a single resin-filling process, the light source-imaging module of the present invention has higher productivity.

DESCRIPTION OF THE PREFERRED EMBODIMENTS

Figure 3:
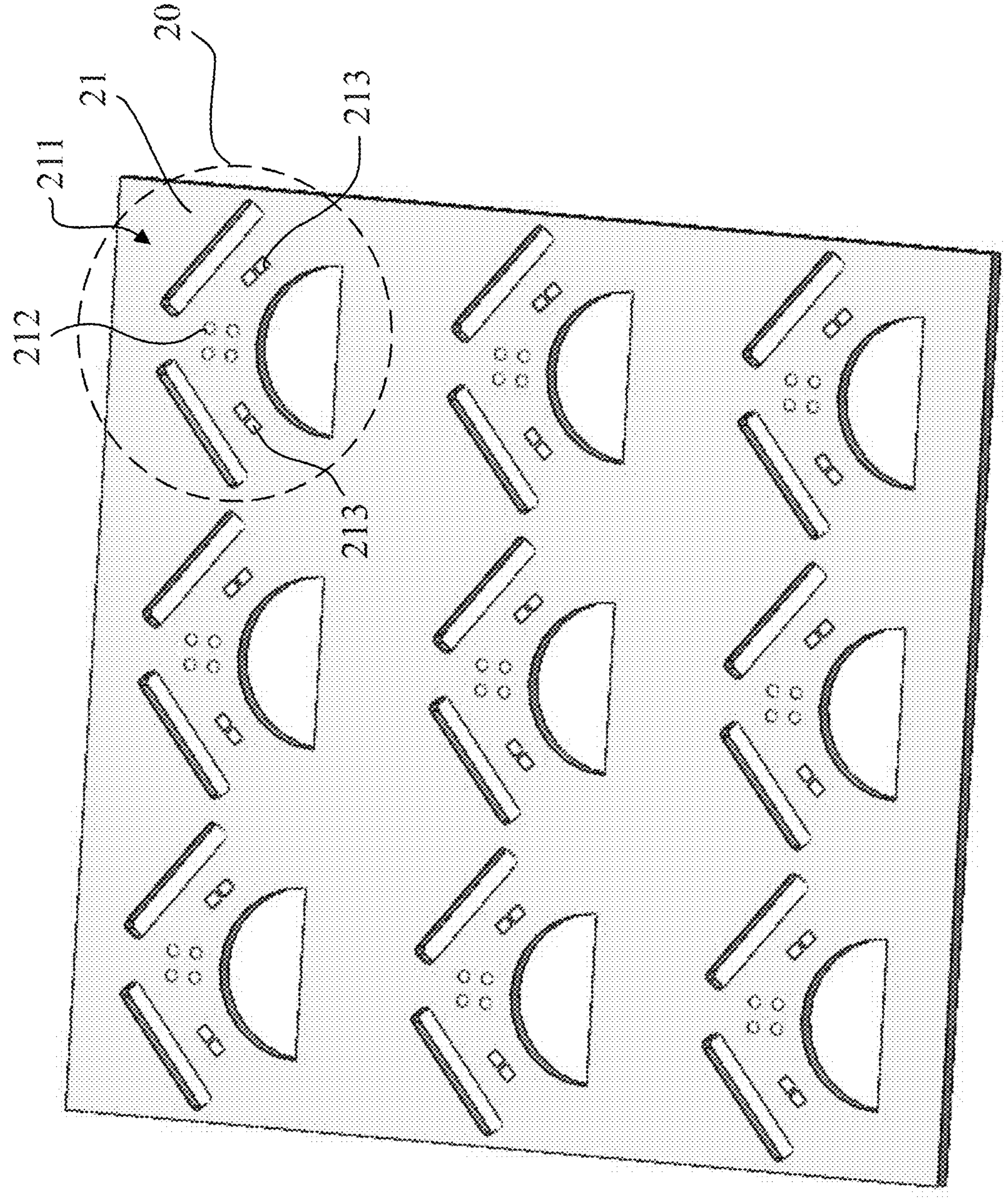
FIGS. 3-9 schematically disclose a method for fabricating an endoscopic light source-imaging module according to one embodiment of the present invention.
Figure 4:
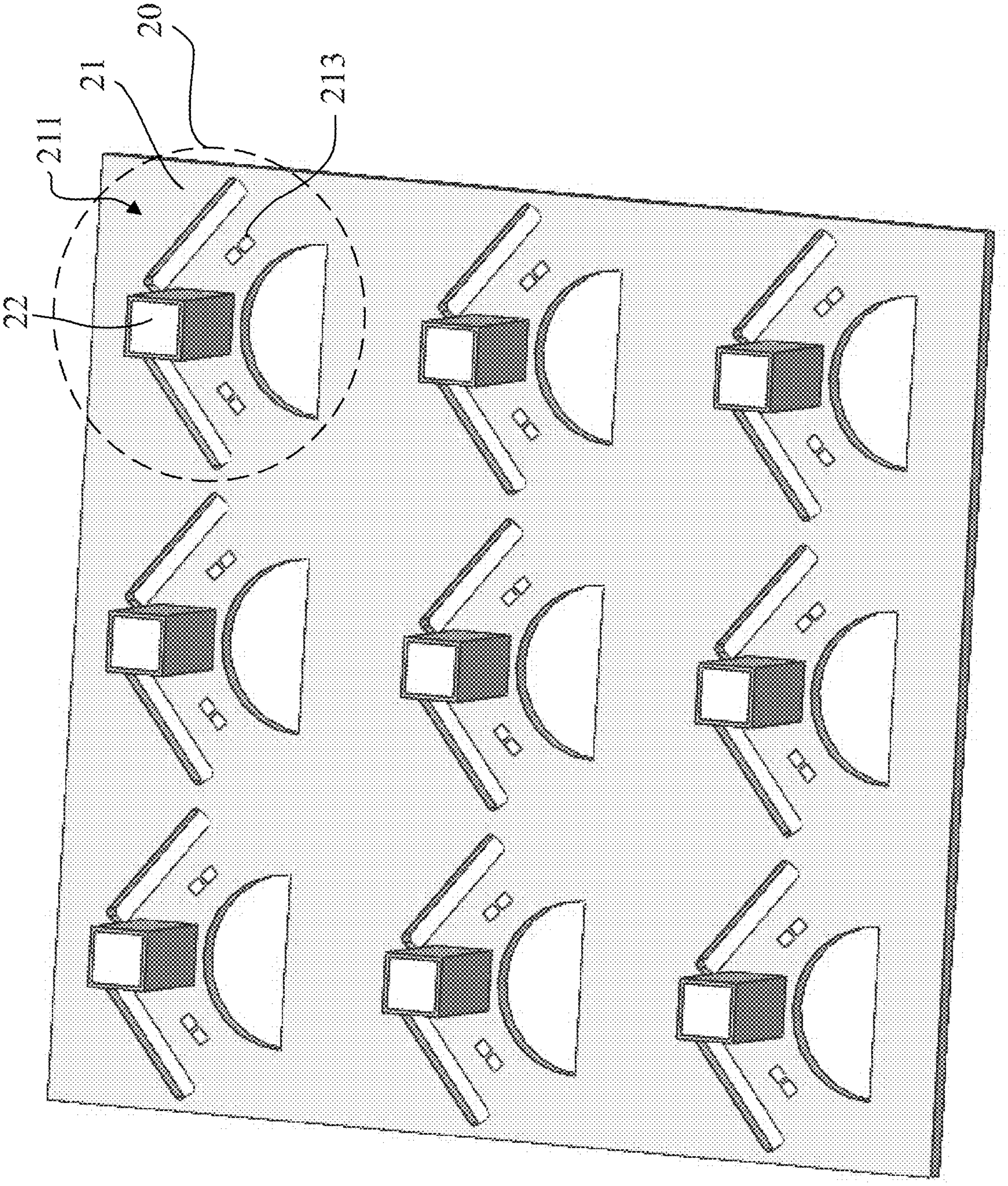
Figure 5:
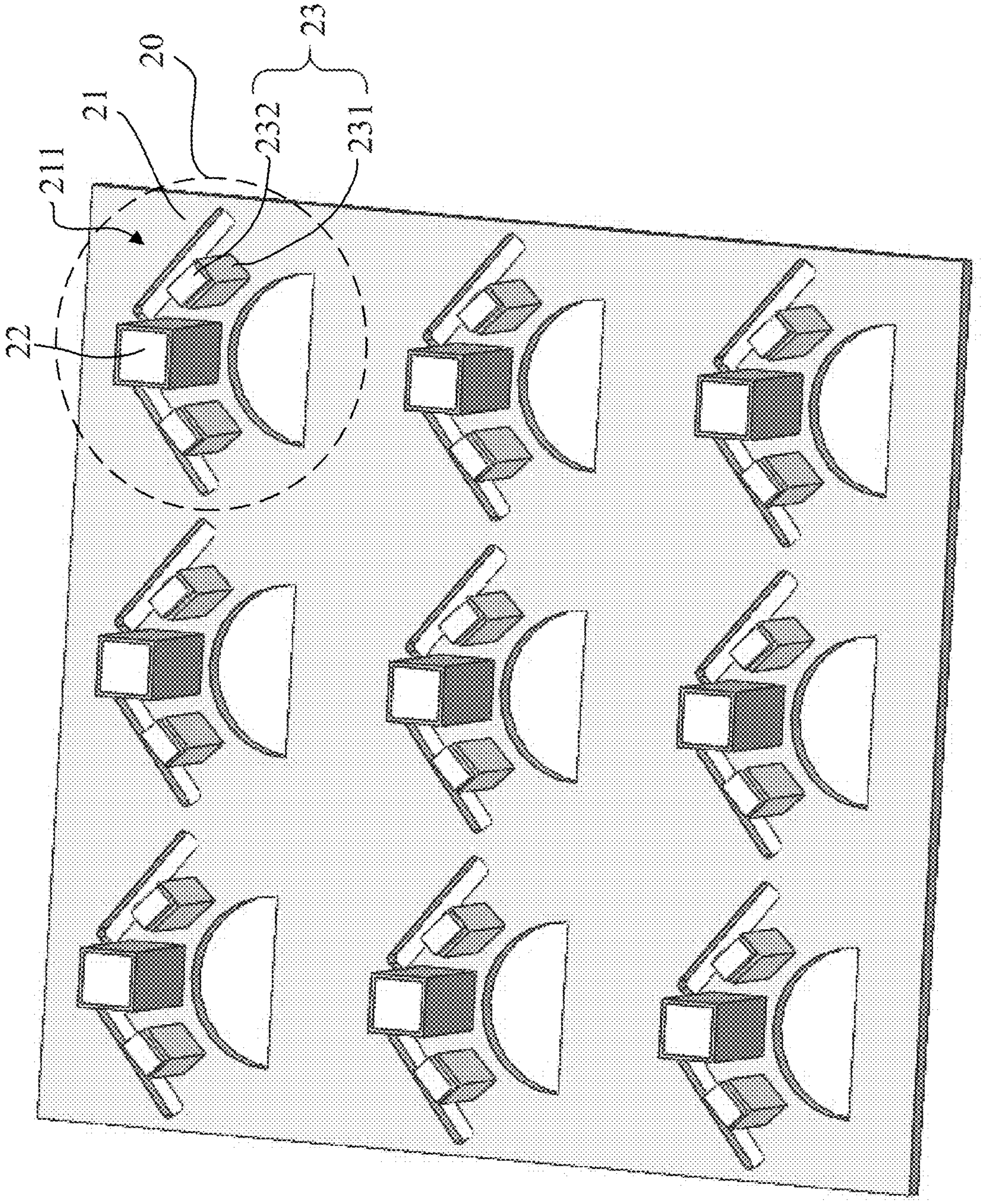

FIGS. 3-9 schematically disclose the method for fabricating a light source-imaging module 20 of an endoscope according to one embodiment of the present invention. As shown in FIG. 3, provide a substrate 21 firstly, wherein the substrate 21 includes a front surface 211, a rear surface (not shown in the drawing), a first metal route 212, and a second metal route 213, and wherein the first metal route 212 and the second metal route 213 extend from the front surface 211 to the rear surface. The substrate 21 may be but is not limited to be a ceramic substrate, a printed circuit board (PCB), or a flexible printed circuit (FPC). Next, as shown in FIG. 4, disposes an image sensor 22 onto the front surface 211 of the substrate 21, and electrically connect the electrodes (not shown in the drawing) on the bottom of the image sensor 22 with the first metal route 212. The electrodes on the bottom of the image sensor 22 may be but is not limited to be a Ball Grid Array (BGA). In one embodiment, the image sensor 22 includes a lens (not shown in the drawing) and a sensing element (not shown in the drawing), wherein the lens is disposed above the sensing element, and the sensing element is electrically connected with the electrodes on the bottom of the image sensor 22. Next, as shown in FIG. 5, after the image sensor 22 has been installed, dispose two illumination modules 23 onto the front surface 211 of the substrate 21. Each illumination module 23 includes a carrier 231 and a light source 232 (such as a light-emitting diode (LED)). The carrier 231 is disposed onto the front surface 211 of the substrate 21, and the electrodes on the bottom of the carrier 231 are electrically connected with the second metal route 213. The light source 232 is disposed to the carrier 231 and electrically connected with the second metal route 213 through the circuit inside the carrier 231. The height of the light source 232 is smaller than or equal to the height of the image sensor 22. The height of the light source 232 may be modified via adjusting the height of the carrier 231. In one embodiment, the carrier 231 is fixed to the substrate 21 beforehand, and then the light source 232 is fixed to the carrier 231 to form the illumination module 23. In another embodiment, the light source 232 is fixed to the carrier 231 to form the illumination module 23 beforehand, and then the illumination module 23 is fixed to the substrate 21.

Figure 1:
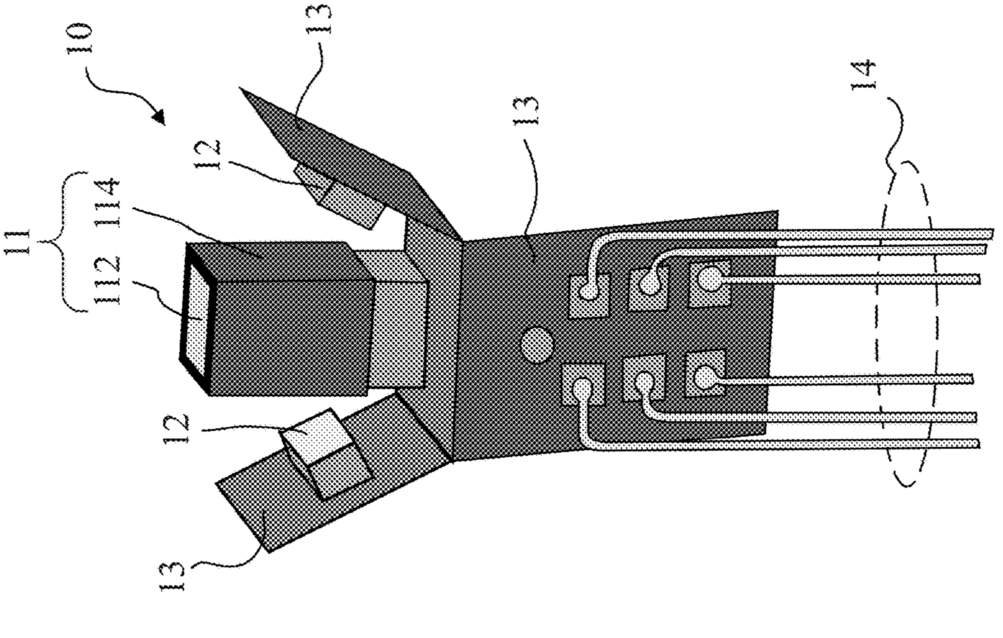
Fig.1 Prior Art
FIG. 1 and FIG. 2 schematically show a conventional light source-imaging module.
Figure 2:
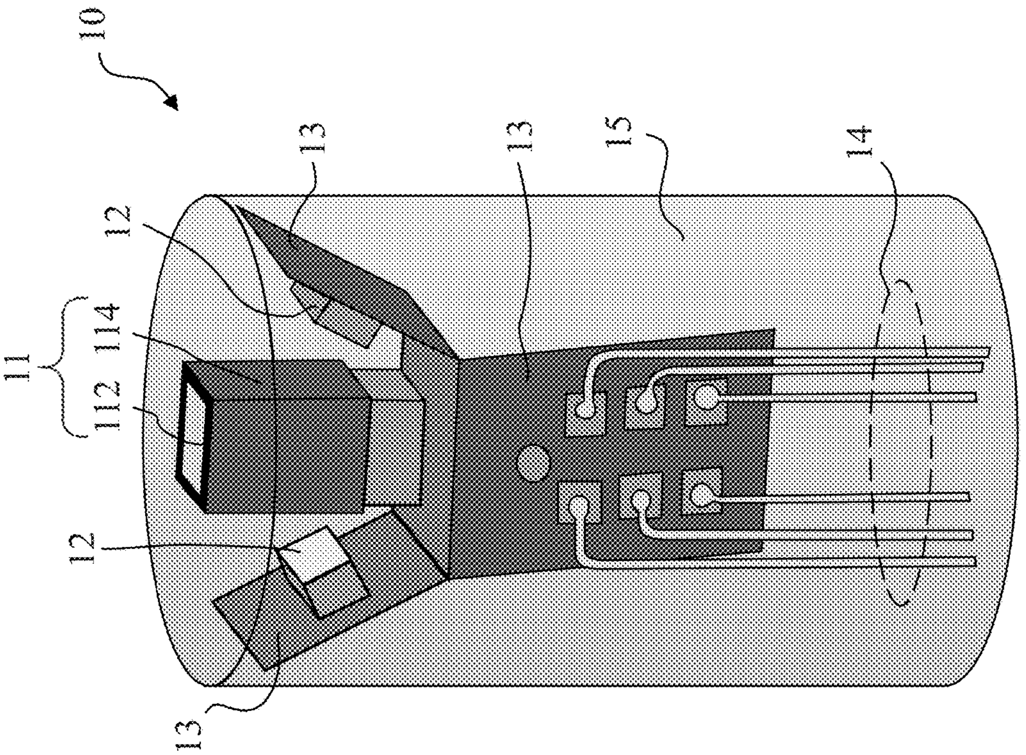
Fig.2 Prior Art

In comparison with the light source-imaging module 10 shown in FIG. 1, the substrate 21 of the light source-imaging module 20 of the present invention needn't be bent to modify the height of the illumination module 23 or the light source 232. Therefore, the light source-imaging module 20 of the present invention is smaller in size and easy for assembly.

In the embodiment mentioned above, the light source-imaging module includes two illumination modules 23. However, the present invention is not limited by the abovementioned embodiment. The illumination modules may be increased or decreased according to requirement.

In the embodiment mentioned above, the method of the present invention installs the image sensor 22 beforehand and then installs the illumination modules 23. However, the present invention is not limited by the abovementioned embodiment. In another embodiment, the method of the present invention may install the illumination modules 23 firstly and then install the image sensor 22. In yet another embodiment, the method of the present invention may install the image sensor 22 and the illumination modules 23 simultaneously.

Figure 6:
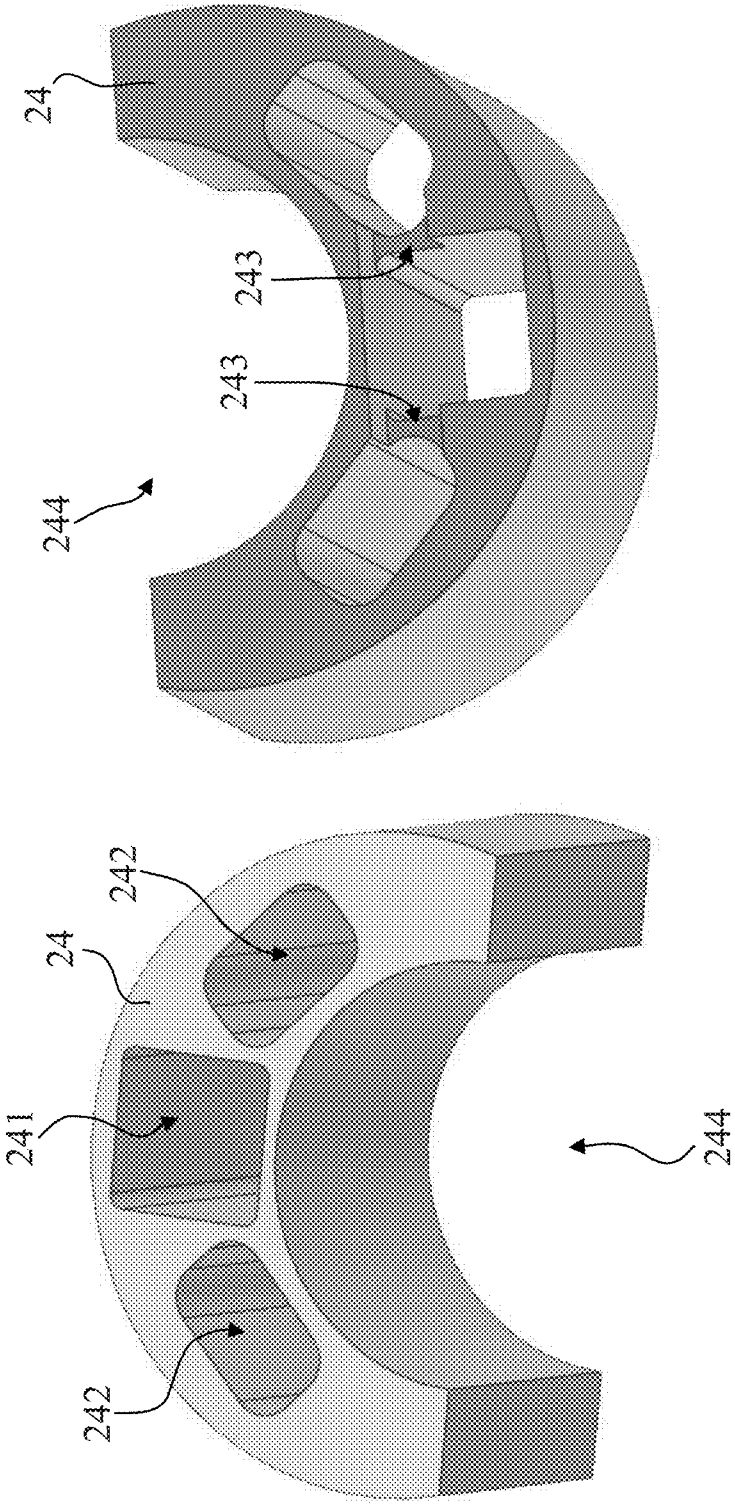

The method of the present invention further comprises a step of providing an opaque single-use mold 24, as shown in FIG. 6. The top view of the single-use mold 24 is shown in the left of FIG. 6. The bottom view of the single-use mold 24 is shown in the right of FIG. 6. The single-use mold 24 includes a first through-hole 241 corresponding to the image sensor 22; two second through-holes 242 respectively corresponding to two illumination modules 23; and at least two runners 243 interconnecting the first through-hole 241 and the second through-holes 242. The number of the second through-holes 242 and the number of the runners 243 may be adjusted according to requirement. For example, while the light source-imaging module 20 only has one illumination module 23, the single-use mold 24 may have only one second through-hole 242 and one runner 243. The single-use mold 24 may be but is not limited to be fabricated in an injection-molding method. In one embodiment, the sidewalls of the second through-holes 242 may be coated or electroplated with reflective films (not shown in the drawing) to function as light-conduction columns. The light-conduction column may concentrate the light emitted by the light source 232 so as to achieve a better illumination effect.

Figure 7:
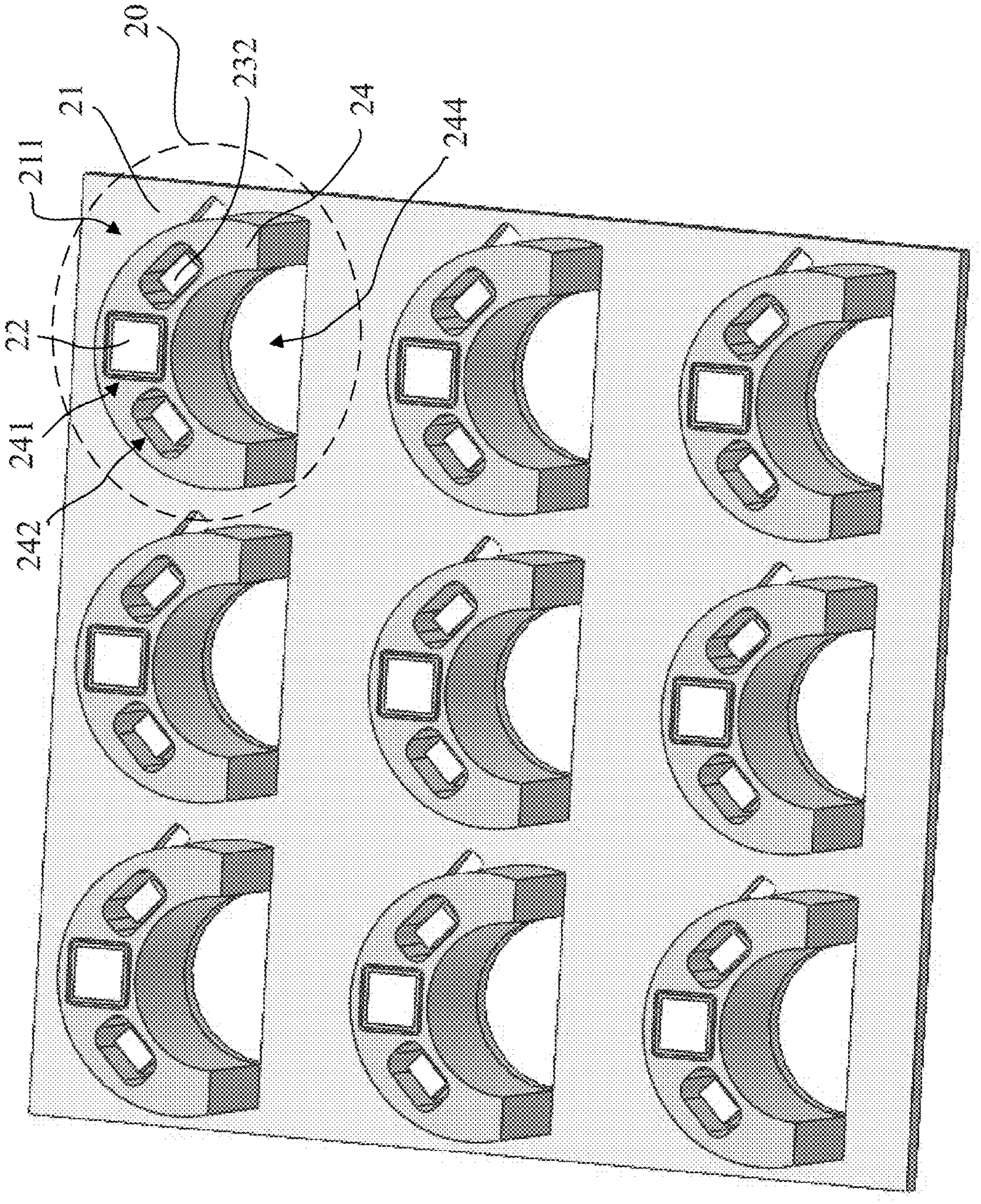

After the image sensor 22 and the illumination module 23 have been installed in the substrate 21, the single-use mold 24 is disposed on the front surface 211 of the substrate 21, as shown in FIG. 7. The first through-hole 241 and the second through-hole 242 of the single-use mold 24 respectively accommodate the image sensor 22 and the illumination module 23. As the single-use mold 24 is made of an opaque material, the light emitted by the light source 232 will not enter the image sensor 22 or the lens to generate stray light.

Figure 8:
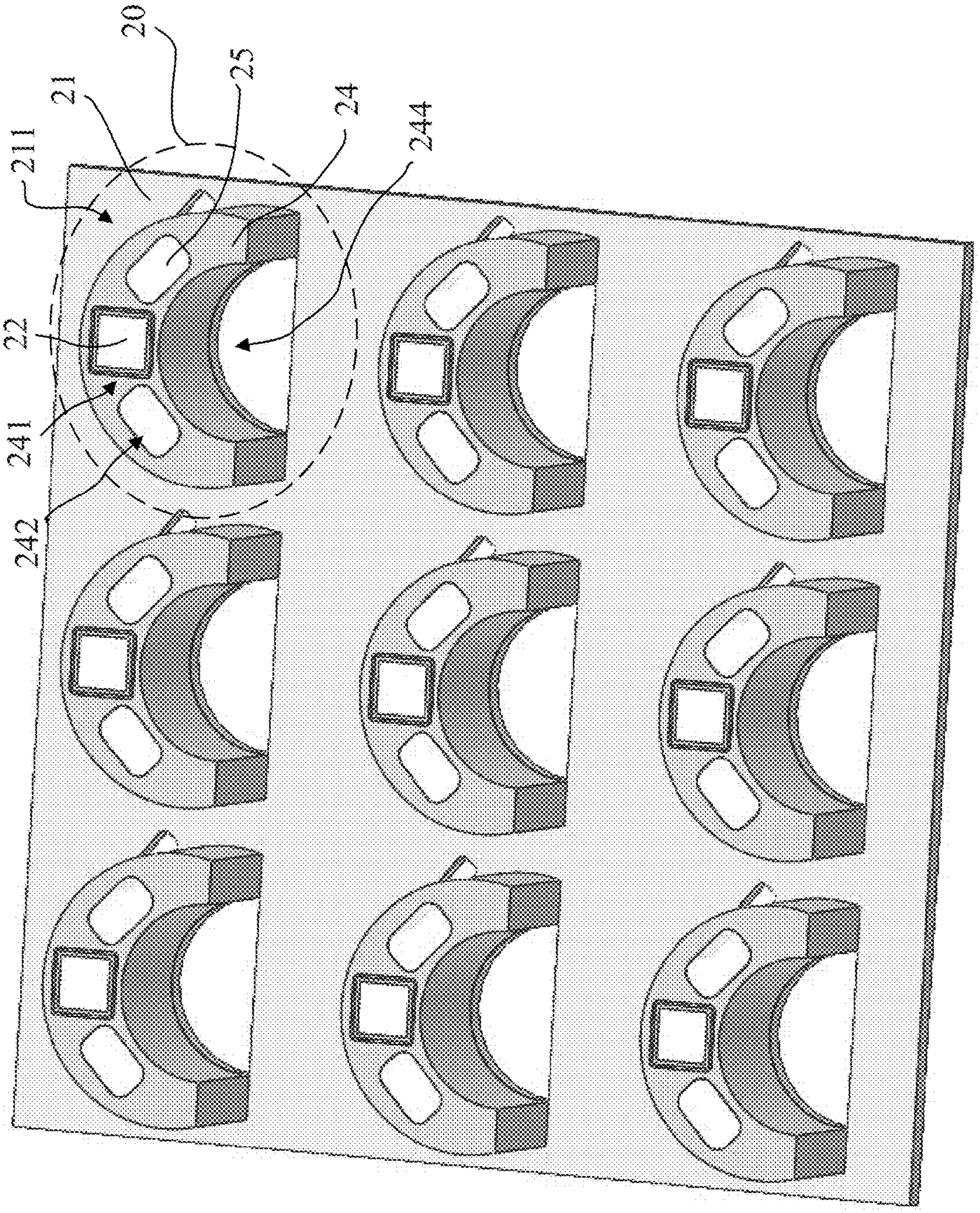
Figure 9:
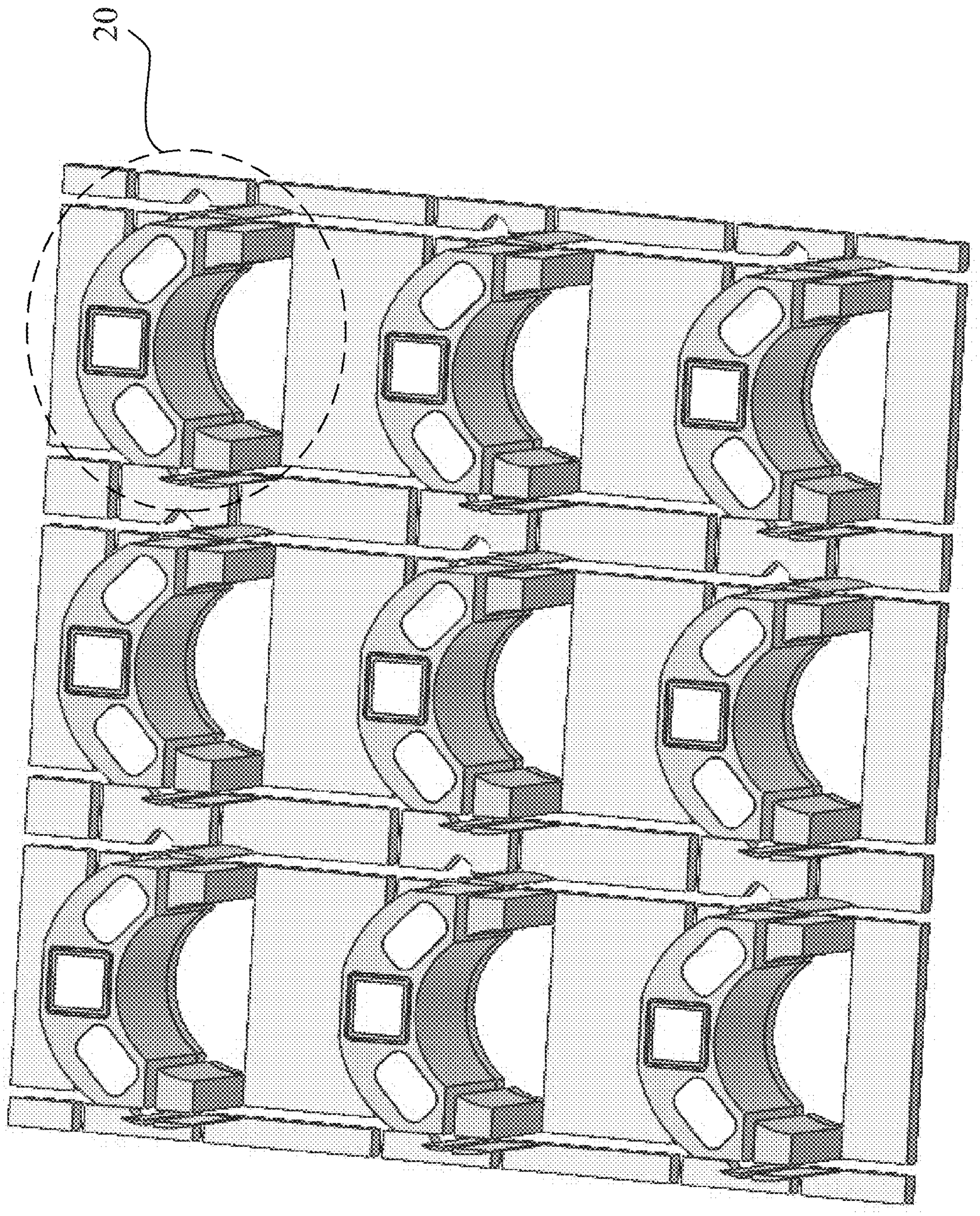

As shown in FIG. 8, after the single-use mold 24 has been installed in the substrate 21, a resin-filling process is performed. A resin 25 is filled via the first through-hole 241 or the second through-hole 242. The resin 25, which is filled via the first through-hole 241 or the second through-hole 242, will flow through the runner 243 to another through-hole. As the resin 25 can flow to all the through-holes via the runners 243, the heights of the resin in all the through-holes are identical. The height of the resin 25 may be adjusted according to requirement. In the case that the resin 25 is a transparent resin, the height of the resin 25 may be larger than the height of the illumination module 23 or the height of the light source 232. However, the height of the resin 25 should not be greater than the height of the image sensor 22 lest the imaging quality be affected. In the case that the resin 25 is a semi-transparent or opaque resin, the height of the resin 25 should not exceed the height of the height of the illumination module 23 or the height of the light source 232 lest the illumination effect be affected. After the resin-filling process is completed, the resin 25 is cured with heat, ultraviolet light, or another curing method, whereby to join together the substrate 21, the image sensors 22, the illumination modules 23 and the single-use molds 24 to form integrated light source-imaging modules 20. Then, a cutting process is performed to obtain the light source-imaging modules 20 of the present invention.

In the present invention, a single resin-filing process is sufficient to fix the image sensor 22 and the illumination module 23 of the light source-imaging module 20 of the present invention. Further, the resin-filling process can also fill the recessed regions (not shown in the drawing) of the image sensor 22 and the illumination module 23. Therefore, the present invention has high production efficiency. If the resin 25 is filled via the second through-hole 242, the resin 25 will be filled into the first through-hole 241 through the runner 243. Therefore, no space needs preserving between the image sensor 22 and the first through-hole 241 to allow the entrance of a needle. In other words, the gap between the image sensor 22 and the first through-hole 241 may be reduced to decrease the size of the light source-imaging module 20.

Figure 10:
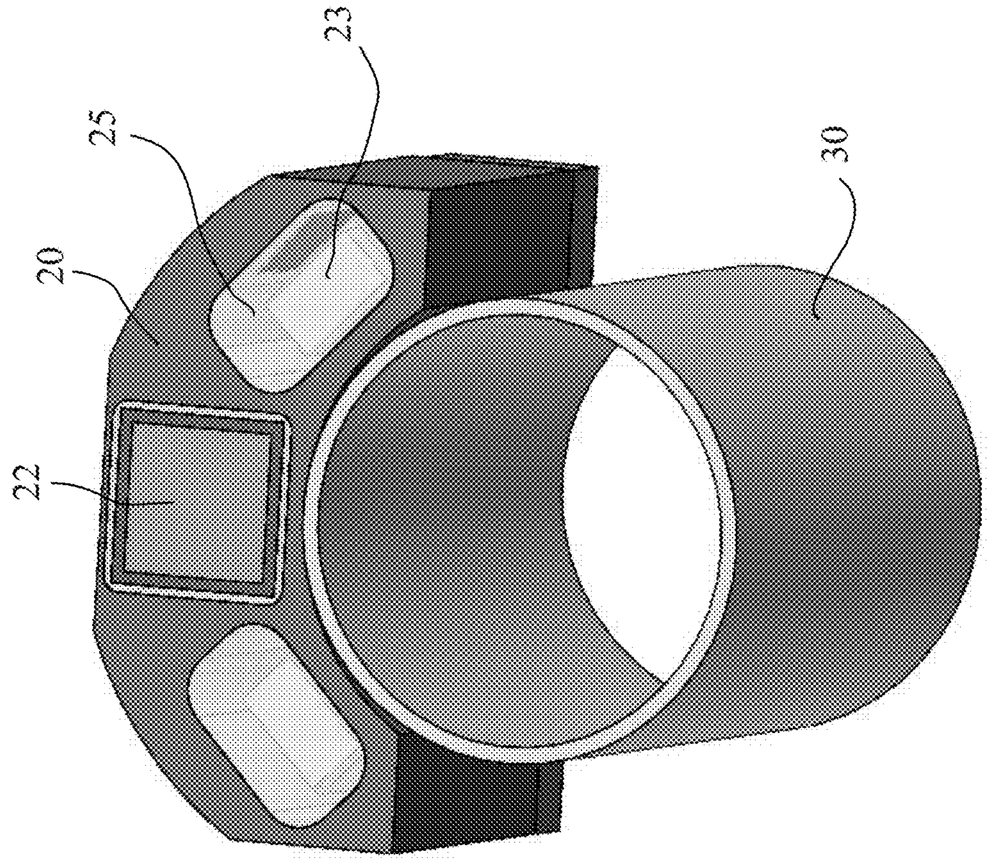
FIG. 10 schematically shows that the light source-imaging module of the present invention is joined with a working channel according to one embodiment of the present invention.
Figure 11:
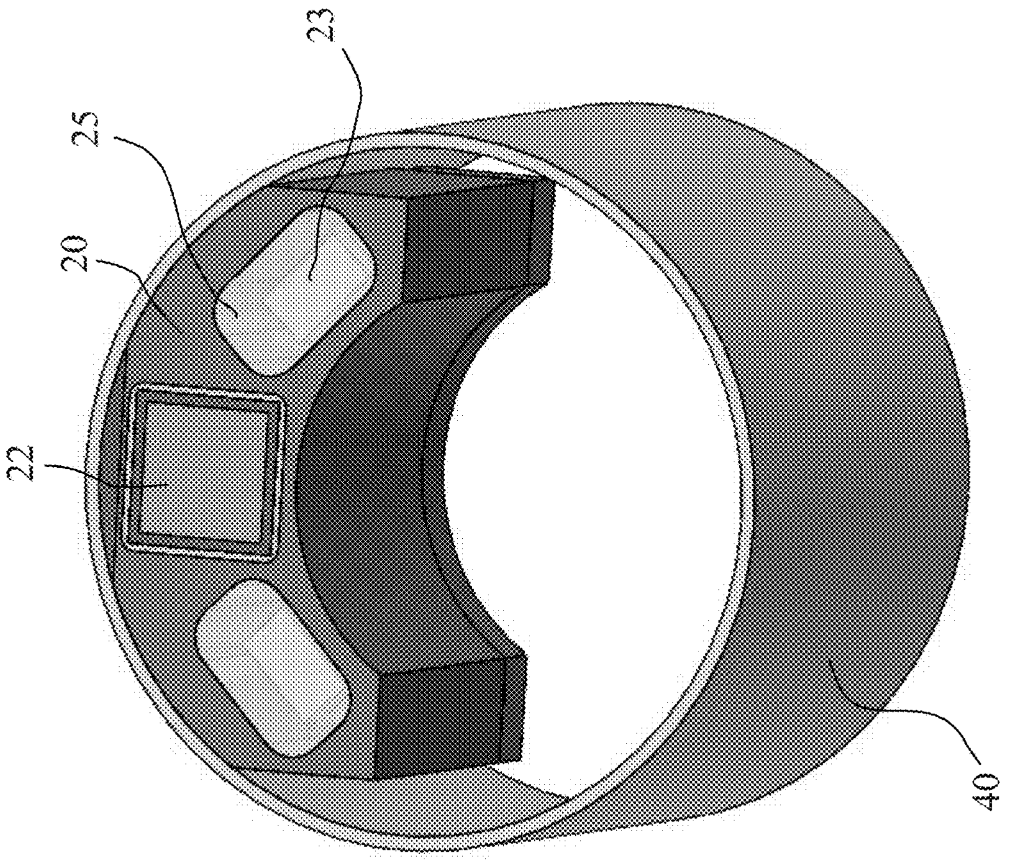
FIG. 11 schematically shows that the light source-imaging module of the present invention is joined with a tip of an endoscope according to one embodiment of the present invention.

In the light source-imaging module 20 of the present invention, a working channel region 244 is reserved in the single-use mold 24, as shown in FIG. 6. While an external working channel 30 is assembled to the light source-imaging module 20, the working channel 30 can be directly sleeved by the working channel region 244. Thus, the difficulty of assemblage is reduced, as shown in FIG. 10.

In the light source-imaging module 20 of the present invention, the contour of the single-use mold 24 matches the shape of the tip 40 of the endoscope. Therefore, the single-use mold 24 can be directly stuck to the inner wall of the tip 40. Hence, the difficulty of positioning and assembling is reduced.

Figure 12:
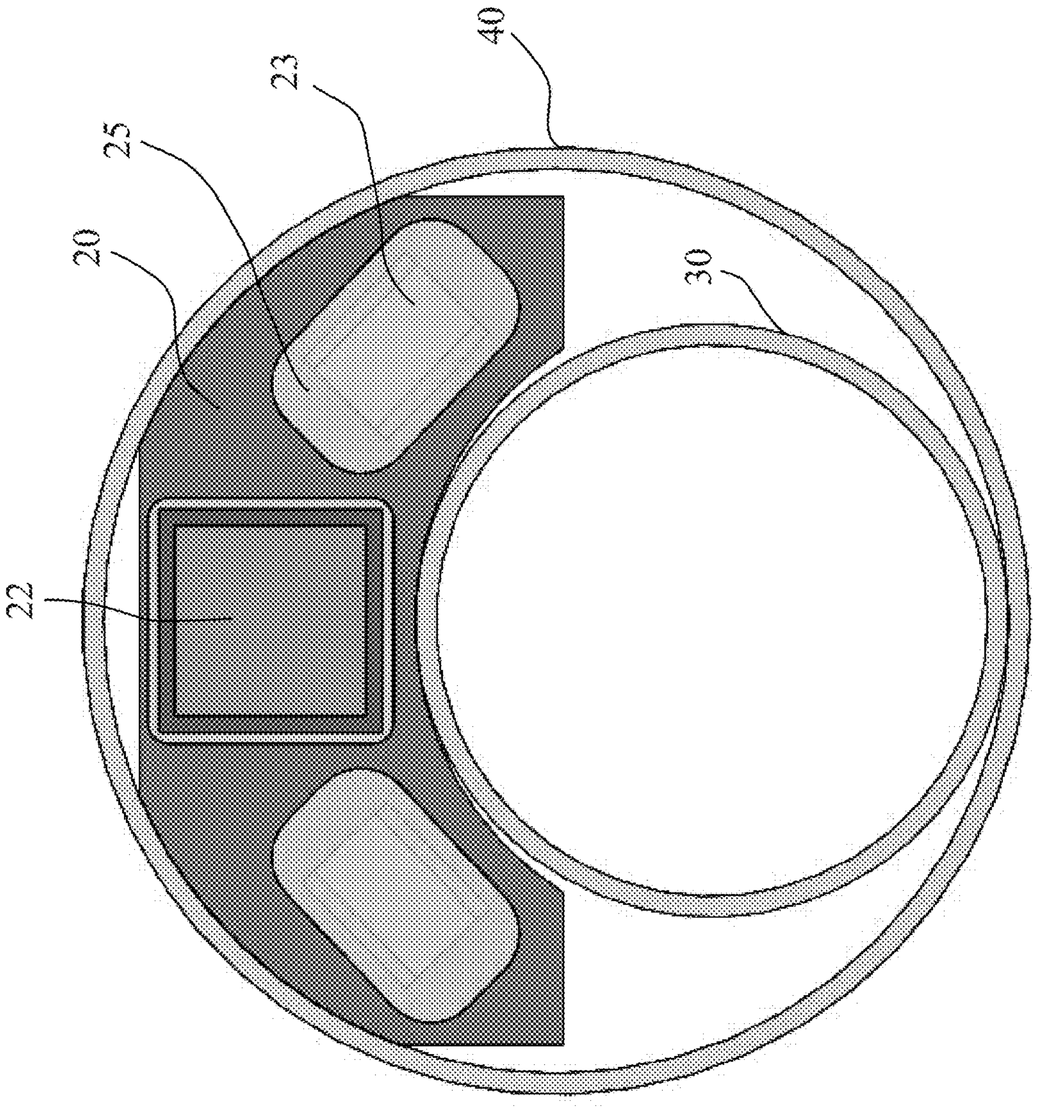
FIG. 12 schematically shows an endoscope using the light source-imaging module according to one embodiment of the present invention.

FIG. 12 schematically shows an endoscope using the light source-imaging module 20 of the present invention. In FIG. 12, the light source-imaging module 20 is stuck to the inner wall of the tip 40, and the working channel 30 is sleeved by the working channel region 244 of the single-use mold 24. Refer to FIGS. 3-5. The control circuit (not shown in the drawing) of the endoscope may be connected with the rear surface of substrate 21 of the light source-imaging module 20 through transmission cables (not shown in the drawing) and then electrically connected with the image sensor 22 and the illumination module 23 through the first metal route 212 and the second metal route 213, whereby the control circuit can control the operation of the image sensor 22 and the illumination module 23.

The embodiments described above are only to demonstrate the present invention but not to limit the scope of the present invention. Any person having ordinary knowledge in the art should be able to make modification or variation according to the technical contents disclosed above to generate embodiments, which would not depart from the spirit of the present invention but should be included by the scope of the present invention.

What is claimed is:

1. A method for fabricating an endoscopic source-imaging module, comprising steps:
- providing a substrate, which includes a front surface, a rear surface, a first metal route, and a second metal route, wherein the first route and the second route extend from the front surface to the rear surface;
- fixing an image sensor onto the front surface and electrically connecting the image sensor with the first metal route;
- disposing an illumination module on the front surface and electrically connecting the illumination module with the second metal route; and
- disposing a single-use mold on the front surface, wherein the single-use mold includes a first through-hole and a second through-hole respectively accommodating the image sensor and the illumination module; the single-use mold also includes a runner interconnecting the first through-hole and the second through-hole.

2. The method according to claim 1, wherein the step of disposing the illumination module on the front surface further includes steps:
- fixing a carrier onto the front surface, and electrically connecting the carrier with the second metal route; and
- fixing a light source onto the carrier to form the illumination module, wherein the light source is electrically connected with the second metal route through the carrier.

3. The method according to claim 1, wherein the single-use mold further includes a working channel region for sleeving a working channel.

4. The method according to claim 1, wherein sidewalls of the second through-hole have reflective films.

5. The method according to claim 1, wherein a height of the image sensor is larger than a height of the illumination module.

6. The method according to claim 5, further comprising steps:
- filling a resin from the first through-hole or the second through hole; and
- curing the resin.

7. The method according to claim 6, wherein the resin is a transparent resin, and a height of the resin is not larger than the height of the image sensor.

8. The method according to claim 6, wherein the resin is an opaque resin or a semi-transparent resin, and a height of the resin is not larger than the height of the illumination module.

* * * * *